US012648810B2

(12) United States Patent
Hansen et al.

(10) Patent No.: US 12,648,810 B2
(45) Date of Patent: *Jun. 9, 2026

(54) MEDICAL DEVICE LOCKING ASSEMBLIES AND METHODS OF USING THE SAME

(71) Applicant: Boston Scientific Medical Device Limited, Galway (IE)

(72) Inventors: Katrina Hansen, Denver, CO (US); John B. Golden, Norton, MA (US); Bernadette Durr, Santa Clara, CA (US); Gregory Hughes, Hanson, MA (US); David Callaghan, Ashland, MA (US); Balaji Aswatha Narayana, Bangalore (IN); Subodh Morey, Ponda (IN); Junaid Shaikh, Surat (IN)

(73) Assignee: Boston Scientific Medical Device Limited, Galway (IE)

( * ) Notice: Subject to any disclaimer, the term of this patent is extended or adjusted under 35 U.S.C. 154(b) by 210 days.

This patent is subject to a terminal disclaimer.

(21) Appl. No.: 18/602,464

(22) Filed: Mar. 12, 2024

(65) Prior Publication Data

US 2024/0216058 A1     Jul. 4, 2024

Related U.S. Application Data

(63) Continuation of application No. 17/137,070, filed on Dec. 29, 2020, now Pat. No. 11,957,408.

(Continued)

(51) Int. Cl.
| | |
|---|---|
| *A61B 18/14* | (2006.01) |
| *A61B 18/00* | (2006.01) |
| *A61B 18/12* | (2006.01) |

(52) U.S. Cl.
CPC ...... *A61B 18/1492* (2013.01); *A61B 18/1206* (2013.01); *A61B 18/1477* (2013.01);
(Continued)

(58) Field of Classification Search
CPC ............ A61B 18/1492; A61B 18/1206; A61B 18/1477; A61B 2018/00178; A61B 2018/00916
See application file for complete search history.

(56) References Cited

U.S. PATENT DOCUMENTS

| | | | |
|---|---|---|---|
| 6,652,506 B2 | 11/2003 | Bowe et al. | |
| 6,699,233 B2 | 3/2004 | Slanda et al. | |

(Continued)

FOREIGN PATENT DOCUMENTS

| | | |
|---|---|---|
| CN | 103200878 A | 7/2013 |
| CN | 105188508 A | 12/2015 |

(Continued)

OTHER PUBLICATIONS

International Search Report and Written Opinion in International Application No. PCT/IB2020/062526, mailed Mar. 11, 2021 (20 pages).

*Primary Examiner* — Linda C Dvorak
*Assistant Examiner* — Abigail Bock
(74) *Attorney, Agent, or Firm* — Bookoff McAndrews, PLLC

(57) ABSTRACT

A medical device that includes a handle, a sheath extending from the handle, and a tool within the sheath and movable relative to the sheath. The handle includes an inner body and an outer body disposed over the inner body. The outer body is movable relative to the inner body. The handle includes a first actuator secured to the tool. The first actuator has an actuated state permitting movement of the tool relative to the sheath in response to moving the outer body relative to the inner body. The handle includes a second actuator secured to the sheath. The second actuator has an actuated state permitting movement of the sheath relative to the tool in response to moving the second actuator relative to the outer body. An unactuated state of the first actuator and an (Continued)

unactuated state of the second actuator prevents movement of the tool relative to the sheath.

20 Claims, 5 Drawing Sheets

Related U.S. Application Data

(60) Provisional application No. 62/957,553, filed on Jan. 6, 2020.

(52) U.S. Cl.
CPC .............. *A61B 2018/00077* (2013.01); *A61B 2018/00178* (2013.01); *A61B 2018/00916* (2013.01)

(56) References Cited

U.S. PATENT DOCUMENTS

| | | | |
|---|---|---|---|
| 8,137,336 | B2 | 3/2012 | Ostrovsky et al. |
| 8,177,773 | B2 | 5/2012 | Ovcharchyn et al. |
| 8,777,929 | B2 | 7/2014 | Schneider et al. |
| 10,849,638 | B2 | 12/2020 | Chu et al. |
| 11,957,408 | B2 * | 4/2024 | Hansen .............. A61B 18/1482 |
| 2009/0062830 | A1 | 3/2009 | Hiraoka |
| 2010/0228084 | A1 | 9/2010 | Sato et al. |
| 2013/0226218 | A1 | 8/2013 | Binmoeller |
| 2016/0045100 | A1 | 2/2016 | Eto |
| 2018/0008127 | A1 | 1/2018 | Tinkham et al. |
| 2018/0103940 | A1 | 4/2018 | Shin et al. |
| 2018/0256200 | A1 | 9/2018 | Benning et al. |
| 2019/0021708 | A1 | 1/2019 | Eto et al. |
| 2019/0328451 | A1 * | 10/2019 | Smith ................ A61B 18/1477 |
| 2021/0177501 | A1 * | 6/2021 | Xia .................... A61B 18/1477 |
| 2021/0186607 | A1 * | 6/2021 | Scott ................. A61B 18/1206 |

FOREIGN PATENT DOCUMENTS

| | | |
|---|---|---|
| CN | 107708577 A | 2/2018 |
| CN | 109069137 A | 12/2018 |
| CN | 109561914 A | 4/2019 |
| JP | 2002503510 A | 2/2002 |
| JP | 2005-204998 A | 8/2005 |
| JP | 2006312054 A | 11/2006 |
| JP | 5797361 B1 | 10/2015 |
| JP | 6562330 B2 | 8/2019 |
| WO | 2018112221 A1 | 6/2018 |

* cited by examiner

MEDICAL DEVICE LOCKING ASSEMBLIES AND METHODS OF USING THE SAME

CROSS-REFERENCE TO RELATED APPLICATIONS

This application is a continuation of U.S. application Ser. No. 17/137,070, filed on Dec. 29, 2020, claims the benefit of priority from U.S. Provisional Application No. 62/957,553, filed on Jan. 6, 2020, each of which is incorporated by reference herein in its entirety.

TECHNICAL FIELD

Various aspects of the disclosure relate generally to medical systems, devices, and related methods. As examples, the disclosure relates to systems, devices, and related methods for securely positioning and/or locking one or more medical devices within a patient during a procedure, among other aspects.

BACKGROUND

Technological developments have given users of medical systems, devices, and methods, the ability to conduct increasingly complex procedures on subjects. One challenge in the field of minimally invasive surgeries such as endoscopy, laparoscopy, and thoracoscopy, among other surgical procedures, is associated with providing control of medical devices with respect to an access and manipulation of such devices during a procedure. Placement of such medical devices within a patient may be difficult. Additionally, maintaining a desired position of a device after placement without requiring continued manual control of the device is unreliable. The limitations on medical devices that facilitate access of other devices into a patient for placement may prolong the procedure, limit its effectiveness, and/or cause injury to the patient due to device failure or breakage.

SUMMARY

Aspects of the disclosure relate to, among other things, systems, devices, and methods for accessing a target treatment site with a medical apparatus having locking assemblies that facilitate positioning of the apparatus, among other aspects. Each of the aspects disclosed herein may include one or more of the features described in connection with any of the other disclosed aspects.

According to an example, a medical device includes a handle, a sheath extending from the handle, and a tool within the sheath and movable relative to the sheath. The handle includes an inner body and an outer body disposed over the inner body. The outer body is movable relative to the inner body. The handle includes a first actuator secured to the tool. The first actuator has an actuated state permitting movement of the tool relative to the sheath in response to moving the outer body relative to the inner body. The handle includes a second actuator secured to the sheath. The second actuator has an actuated state permitting movement of the sheath relative to the tool in response to moving the second actuator relative to the outer body. An unactuated state of the first actuator and an unactuated state of the second actuator prevents movement of the tool relative to the sheath.

Any of the medical devices described herein may have any of the following features. Longitudinal movement of the second actuator moves the sheath longitudinally relative to the inner body and the outer body. The first actuator inhibits movement of the outer body relative to the inner body when in the unactuated state. The second actuator inhibits movement of the sheath relative to the inner body and the outer body when in the unactuated state. The inner body includes a plurality of teeth extending along an exterior of the inner body. The first actuator includes one or more teeth configured to engage one or more of the plurality of teeth of the inner body when in the unactuated state. Further including a first spring disposed between the first actuator and the outer body, wherein the first spring is configured to bias the first actuator radially outward relative to the outer body and maintain the first actuator in the unactuated state. The first actuator is in the actuated state where the one or more teeth of the first actuator are spaced apart from all of the plurality of teeth of the inner body, when a radially inward force that exceeds a bias of the first spring is applied to the first actuator. The inner body includes a plurality of teeth extending along an exterior of the inner body. The second actuator includes one or more teeth configured to engage one or more of the plurality of teeth of the inner body when in the unactuated state. Further including a second spring disposed between the second actuator and the outer body, wherein the second spring is configured to bias the second actuator radially outward relative to the outer body and maintain the second actuator in the unactuated state. The second actuator is in the actuated state where the one or more teeth of the second actuator are spaced apart from all of the plurality of teeth of the inner body, when a radially inward force that exceeds a bias of the second spring is applied to the second actuator. The first actuator includes one or more first teeth configured to engage one or more of the plurality of teeth of the inner body when in the unactuated state. Further including a first spring disposed between the first actuator and the outer body, wherein the first spring is configured to bias the first actuator radially outward relative to the outer body and maintain the first actuator in the unactuated state. The first actuator is in the actuated state where the one or more teeth of the first actuator are spaced apart from all of the plurality of teeth of the inner body, when a radially inward force that exceeds a bias of the first spring is applied to the first actuator. The handle further includes an active connector configured to communicatively couple the sheath to an electrosurgical generator, and the sheath includes an electrically conductive material, wherein the active connector is coupled to the sheath through the second actuator.

According to another example, a medical device includes a sheath, a tool within the sheath and movable relative to the sheath, a handle disposed over the sheath and movable relative to the sheath. The handle including an inner body, an outer body disposed over the inner body and movable relative to the inner body, a first actuator configured to move the tool relative to the sheath and the inner body when in an actuated state, and a second actuator configured to move the sheath relative to the inner body, the outer body, and the tool when in an actuated state. The first actuator and the second actuator engage the inner body when in an unactuated state such that movement of the tool and the sheath are inhibited.

Any of the medical devices described herein may have any of the following features. Further including a plurality of teeth extending along an exterior of the inner body, and one or more teeth extending from the first actuator and configured to engage one or more of the plurality of teeth of the inner body when in the unactuated state. Further including a first spring disposed between the first actuator and the outer body that is configured to bias the first actuator radially outward relative to the outer body to maintain the first actuator in the unactuated state. The first actuator is in the actuated state where the one or more teeth of the first actuator are spaced apart from all of the plurality of teeth of the inner body, when a radially inward force that exceeds a bias of the first spring is applied to the first actuator. Further including one or more teeth extending from the second actuator and configured to engage one or more of the plurality of teeth of the inner body when in the unactuated state. Further including a second spring disposed between the second actuator and the outer body that is configured to bias the second actuator radially outward relative to the outer body to maintain the second actuator in the unactuated state. The second actuator is in the actuated state where the one or more teeth of the second actuator are spaced apart from all of the plurality of teeth of the inner body, when a radially inward force that exceeds a bias of the second spring is applied to the second actuator.

According to another example, a medical instrument includes a sheath and a tool movable within the sheath. The medical instrument includes a medical device including a first actuator, a second actuator, an outer body, and an inner body movable within the outer body. The first actuator is operable to allow movement of the tool relative to the sheath, and the outer body relative to the inner body when in an actuated state. The second actuator is operable to allow movement of the sheath relative to the tool, and relative to the outer body and the inner body when in an actuated state. The first actuator and the second actuator are collectively operable to inhibit movement of the tool relative to the sheath and the sheath relative to the tool and the inner body when in an unactuated state.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

4

Figure 8:
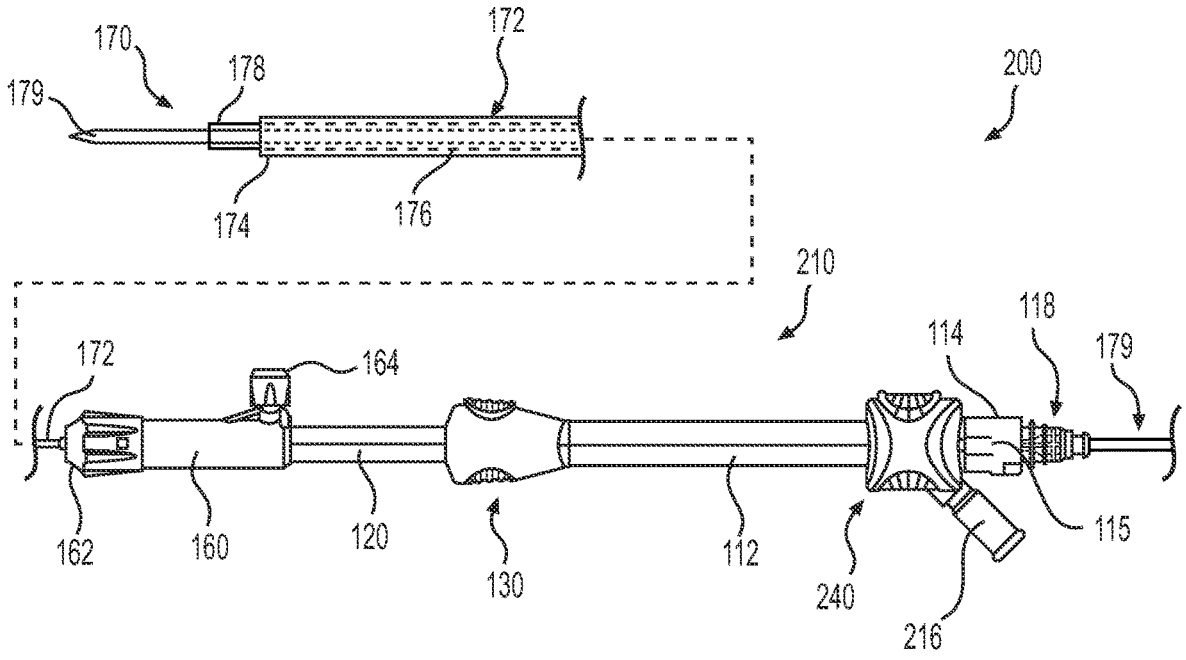
FIG. 8 is a side view of another exemplary medical system including a medical device and a medical instrument, with the medical device including a first actuator and a second actuator, according to aspects of this disclosure.
Figure 9:
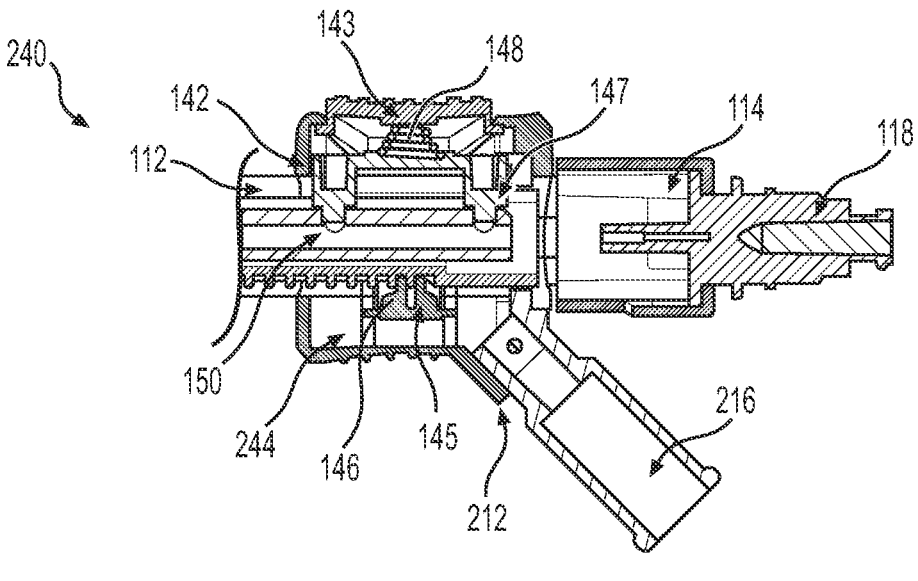
Figure 10:
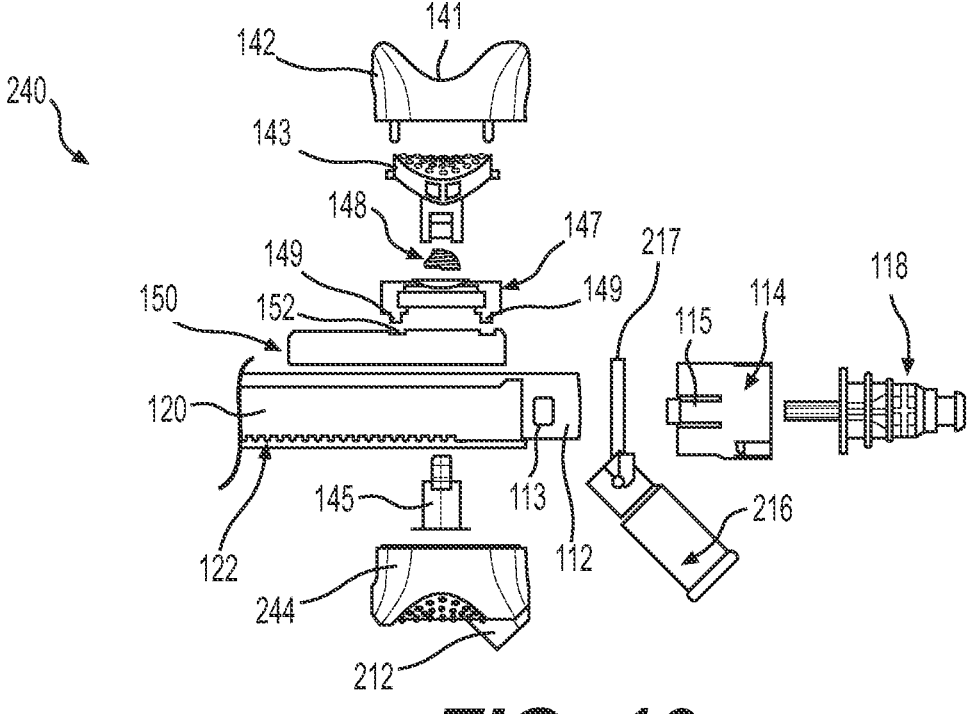

FIG. 9 is a cross-sectional side view of the second actuator of the medical device of FIG. 8 in a locked state, according to aspects of this disclosure; and FIG. 10 is an exploded side view of the second actuator of the medical device of FIG. 8, according to aspects of this disclosure.

DETAILED DESCRIPTION

Examples of the disclosure include systems, devices, and methods for controlling one or more components of a medical instrument at a target site within the body, where the components generally require manual control or manipulation to access a target site, among other aspects. Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may be used to facilitate control and positioning of tools/devices of a medical instrument at a target treatment site by providing one or more mechanisms and/or assemblies for securing said tools/devices at the target treatment site. For instance, some examples utilize a first actuator and a second actuator on a medical device for selective control and/or manipulation of components of a medical instrument received within the medical device. The medical device may include an inner body that defines a lumen configured to receive the medical instrument therein, and an outer body disposed over the inner body and movable relative to the inner body. The medical instrument may include a sheath and a tool disposed within the sheath. The first actuator may be positioned on the outer body and coupled to the tool of the medical instrument (e.g., an access cannula, a needle, etc.) and the second actuator may be positioned on the outer body and coupled to the sheath of the medical instrument. The first actuator may be configured to move the tool relative to the sheath and the outer body relative to the inner body, and the second actuator may be configured to move the tool relative to the sheath and the second actuator relative to the outer body.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). The device and related methods may be used laparoscopically or endoscopically, or in any other open or minimally invasive procedure, including thorascopic and ENT procedures. Reference will now be made in detail to examples of the present disclosure described above and illustrated in the accompanying drawings. Wherever possible, the same reference numbers will be used throughout the drawings to refer to the same or like parts.

Figure 1:
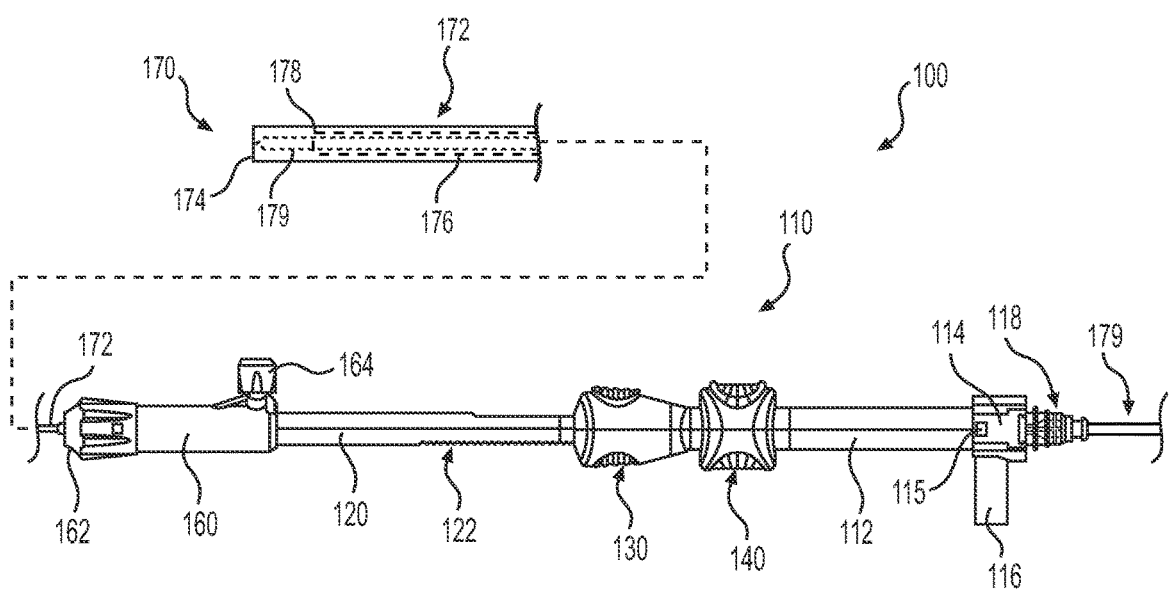
FIG. 1 is a side view of an exemplary medical system including a medical device and a medical instrument, with the medical device having a first actuator and a second actuator, according to aspects of this disclosure.

FIG. 1 shows a schematic depiction of an exemplary medical system 100. The medical system 100 may include a medical device 110 and a medical instrument 170. In the example, the medical device 110 has a handle that includes an outer body 112 and an inner body 120, with the outer body 112 having a longitudinal length that defines a lumen which is sized, shaped, and configured to receive the inner body 120. As described in greater detail herein, the outer body 112 is configured to move relative to the inner body 120, and vice versa, the inner body 120 is configured to move relative to the outer body 112. The inner body 120 of the medical device 110 has a longitudinal length that defines a lumen which is sized, shaped, and configured to receive the medical instrument 170.

In the example, the inner body 120 includes a rack portion having a plurality of teeth 122 extending along an exterior surface of the inner body 120. The plurality of teeth 122 extend along a predetermined portion (e.g., longitudinal length) of the inner body 120 that corresponds to a range of motion of the outer body 112 relative to the inner body 120. Accordingly, it should be understood that the rack portion including the plurality of teeth 122 may extend along various other suitable lengths and/or surfaces of the inner body 120 than that shown and described herein without departing from a scope of this disclosure, from only a portion of the longitudinal length of the inner body 120 up to, and including an entirety of a longitudinal length of the inner body 120. The medical device 110 may further include an end cap 114, an active pin or connector 116, and a rotation assembly 118 disposed on and/or coupled to the outer body 112. The end cap 114 of the medical device 110 may be positioned at a proximal end of the outer body 112 and is configured to enclose a lumen of the outer body 112.

Further, the medical instrument 170 of the medical system 100 may include a catheter having a sheath 172, a cannula 176, and a needle 179. The cannula 176 may be disposed within a lumen of the sheath 172, and the needle 179 may be disposed within a lumen of the cannula 176, and may extend at least partially outward from the tip 178 of the cannula 176. Although the needle 179 is described herein, it should be understood that the exemplary medical instrument 170 of this disclosure may be a tool having any end effector, including but not limited to a grasper, a snare, forceps, scissors, and the like. In the example, a position, orientation, and/or configuration of the needle 179 relative to the cannula 176 is fixed such that a distal end of the needle 179 is maintained at an extended position relative to the tip 178 of the cannula 176. The sheath 172 includes a tip 174 and has a longitudinal length defined by the distance between the tip 174 and a proximal end of the sheath 172 (not shown). The cannula 176 of the medical instrument 170 includes a tip 178 and has a longitudinal length defined by the distance between the tip 178 and a proximal end of the cannula 176 (not shown). As described in greater detail herein, one or more components of the medical device 110 may be configured and operable to position the medical instrument 170 relative to a target treatment site within a patient (e.g., patient anatomy). For example, the medical instrument 170 may be operable to puncture a target treatment site with the needle 179, when the needle 179 is extended distally of the tip 174, or may be able to perform a medical procedure with a desired end effector.

Still referring to FIG. 1, in some examples, the medical instrument 170 may be operable to facilitate access of one or more tools and/or devices to a target treatment site with the cannula 176, including and/or in addition to the needle 179. In this instance, upon removal of the needle 179 from a lumen of the cannula 176, one or more additional tools and/or devices may be received through a lumen of the cannula 176 and extended outwardly and distally therefrom via the tip 178 of the cannula 176. Further, in some examples, the medical instrument 170 may be operable to electrosurgically dilate a target treatment site with the sheath 172. In this instance, the sheath 172 includes an electrosurgical sheath and the tip 174 includes an electrosurgical tip. It should be understood that, in other examples, the medical instrument 170 may include various other suitable tools, configurations, hypotubes and/or components than those shown and described herein. By way of illustrative example, in some examples the medical instrument 170 may include an electrosurgical end (e.g., cystotome needle) that omits the tip 178, such as, for example, for delivering a stent during a procedure. In other examples the medical instrument 170 omits components configured for electrical activation.

Figure 2:
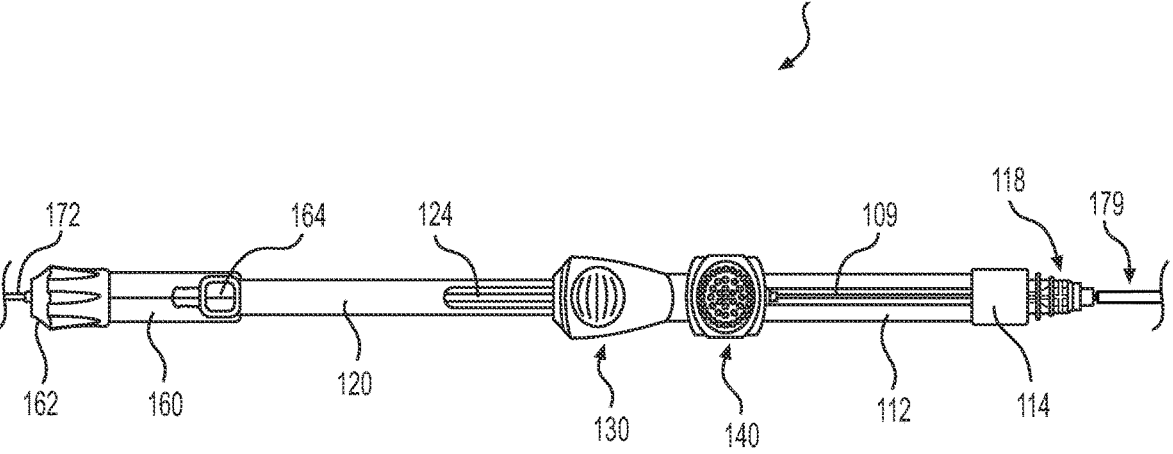
FIG. 2 is a top view of the medical device of FIG. 1, according to aspects of this disclosure.

As seen in FIG. 2, the outer body 112 of the medical device 110 may include one or more slots 109 disposed through the outer body 112. In this instance, a lumen of the outer body 112 may be accessible via the one or more slots 109. In the example, the outer body 112 includes a pair of slots 109 formed along a longitudinal length of the outer body 112 and positioned along opposing sides of the outer body 112, such as, for example, along a top surface and a bottom surface of the outer body 112. As described in greater detail below, the one or more slots 109 of the outer body 112 are configured to slidably receive one or more components of the medical device 110 therein, such as, for example, a second actuator 140.

In the example, the inner body 120 of the medical device 110 may further include one or more slots 124 disposed through the inner body 120. In this instance, a lumen of the inner body 120 may be accessible via the one or more slots 124. In the example, the inner body 120 includes a pair of slots 124 formed along a longitudinal length of the inner body 120 and positioned along opposing sides of the inner body 120, such as, for example, along a top surface and a bottom surface of the inner body 120. As described in greater detail below, the one or more slots 124 of the inner body 120 are configured to slidably receive one or more components of the medical device 100 therein, such as, for example, a first actuator 130 and/or the second actuator 140. As shown, the one or more slots 109 of the outer body 112 are radially aligned with the one or more slots 124 of the inner body 120, however, it should be understood that in other examples the slots 109 may be radially offset relative to the slots 124.

Figure 3:
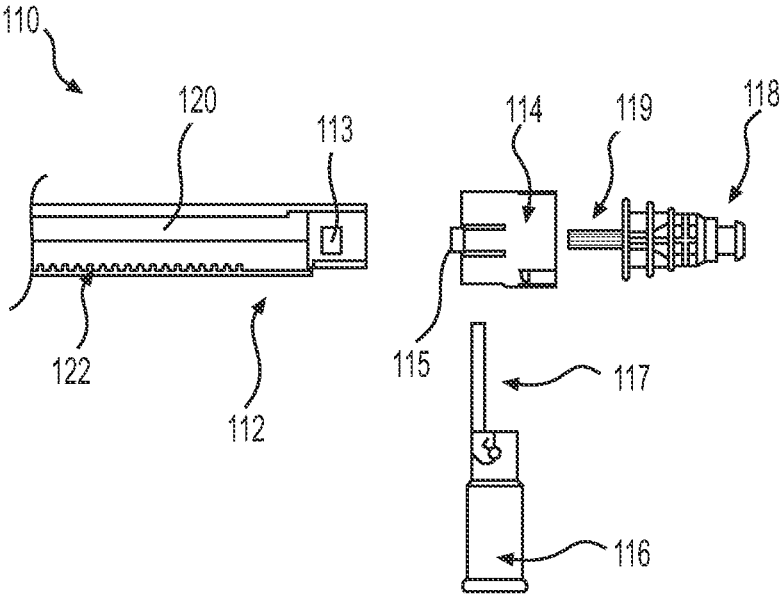
FIG. 3 is a partial and exploded side view of the medical device of FIG. 1, according to aspects of this disclosure.

Referring now to FIG. 3, the end cap 114 may include one or more snap features 115 disposed along an exterior of the end cap 114 for coupling the end cap 114 to the outer body 112. In the example, the one or more snap features 115 are configured to engage and snap into an aperture 113 formed on a distal end of the outer body 112. The active pin 116 of the medical device 110 may be coupled to the end cap 114, and the active pin 116 is operable to establish electrical communication with the medical instrument 170 disposed within a lumen of the inner body 120. For example, the active pin 116 may include a connector 117 extending from the active pin 116 that is configured to be received within the end cap 114 and operable to communicatively couple the active pin 116 to one or more components of the medical instrument 170, such as, for example, the electrosurgical sheath 172. In this instance, the active pin 116 is operable to establish electrosurgical connection between the electrosurgical sheath 172 of the medical instrument 170 and an ancillary device, such as, for example, an electrosurgical generator, a power source, a controller, or the like (not shown) operable to generate high frequency electric or RF current.

Still referring to FIG. 3, the rotation assembly 118 of the medical device 110 may be coupled to the end cap 114 at a proximal end of the end cap 114 opposite of the outer body 112. For instance, the rotation assembly 118 may include a coupling feature 119 that is received within the end cap 114 for securing the rotation assembly 118 thereto. In this instance, with the rotation assembly 118 coupled to the end cap 114, and the end cap 114 coupled to the outer body 112 via the snap feature 115, it should be appreciated that the end cap 114 and the rotation assembly 118 may move simultaneously with the outer body 112. In the example, at least a portion of the rotation assembly 118 extends outwardly and proximally from the end cap 114 to facilitate access of the rotation assembly 118 to a user of the medical system 100. The coupling feature 119 of the rotation assembly 118 is further configured to engage a proximal end of the medical instrument 170 disposed within a lumen of the inner body 120 when the coupling feature 119 is received within the end cap 114. The rotation assembly 118 engages and is coupled to the cannula 176 of the medical instrument 170 within the inner body 120.

In the example, the rotation assembly 118 is configured to move (e.g., rotate) relative to the end cap 114, the outer body 112, and the inner body 120. Accordingly, with the rotation assembly 118 coupled to the medical instrument 170 via the coupling feature 119, the rotation assembly 118 is operable to move (e.g., rotate) the cannula 176 of the medical instrument 170 relative to the medical device 110. For example, the rotation assembly 118 rotates the medical instrument 170 within lumens of the outer body 112 and the inner body 120. As described above, with the needle 179 disposed within the cannula 176, it should be appreciated that the rotation assembly 118 is operable to move (e.g., rotate or actuate) the needle 179 with the cannula 176, together, relative to the outer body 112 and the inner body 120. In some examples, the rotation assembly 118 may include a rotatable knob, wheel, and/or various other suitable actuators for rotating the cannula 176 of the medical instrument 170 relative to the medical device 110. It should be appreciated that, in other examples, the rotation assembly 118 may engage other and/or additional components of the medical instrument 170 than those shown and described herein.

Although not shown, it should be appreciated that the rotation assembly 118 includes a lumen extending through the rotation assembly 118 and the coupling feature 119. The lumen of the rotation assembly 118 may be sized, shaped, and configured to receive one or more tools and/or devices of the medical instrument 170 therethrough, such as, for example, the needle 179. In the example, with the rotation assembly 118 coupled to the cannula 176, it should be understood that a lumen of the rotation assembly 118 may be aligned with, coupled to, and/or in communication with a lumen of the cannula 176. Accordingly, the rotation assembly 118 may be configured and operable to facilitate access to a lumen of the cannula 176, to the tip 178 of the cannula 176. As seen in FIGS. 1-2, a proximal end of the needle 179 is received through the rotation assembly 118 and a sharp distal end of the needle 179 may be positioned adjacent to the tip 178 of the cannula 176. In some examples, the needle

179 may be removed from a lumen of the cannula 176 by extracting the needle 179 proximally through a lumen of the rotation assembly 118.

Referring back to FIG. 1, the medical device 110 may further include the first actuator 130 and the second actuator 140 positioned on the outer body 112. In the example, the first actuator 130 and the second actuator 140 are disposed over the outer body 112 and are movable relative to one another. As described in further detail herein, the first actuator 130 is secured and/or coupled to the outer body 112 and is configured to move the outer body 112 relative to the inner body 120 in response to actuation of the first actuator 130. In the example, the first actuator 130 is integral with the outer body 112 such that the first actuator 130 forms a unitary structure with the outer body 112. However, it should be appreciated that a unitary structure of the first actuator 130 and the outer body 112 may not be required in other examples. Further, the second actuator 140 is secured and/or coupled to the inner body 120 and is configured to move the inner body 120 relative to the outer body 112 in response to actuation of the second actuator 140. For instance, the second actuator 140 may be coupled to the inner body 120 through the outer body 112, such as, for example, via one or more of the pair of slots 109 formed on the outer body 112.

The medical device 110 further includes a distal housing 160 positioned at a distal end of the inner body 120 opposite of the outer body 112. The distal housing 160 of the medical device 110 defines a lumen that is sized, shaped, and configured to receive one or more components of the medical device 110 therethrough, such as, for example, at least a portion of the inner body 120, the medical instrument 170, and the like. The distal housing 160 of the medical device 110 may further include a housing tip 162 and a screw (fastener) 164. In the example, the housing tip 162 includes an opening that is sized and shaped to facilitate an exit of the medical instrument 170 from a lumen of the distal housing 160 and/or a lumen of the inner body 120. The screw 164 is configured to engage an exterior surface of the inner body 120 (i.e., a portion of which is disposed within a lumen of the distal housing 160) to securely couple the inner body 120 to the distal housing 160. In this instance, the screw 164 is movable (e.g., rotatable) relative to the distal housing 160 to selectively engage and/or disengage the inner body 120 received therein. It should be appreciated that various other suitable fastening elements, clamps, pins, and the like are also contemplated without departing from a scope of this disclosure.

Figure 4:
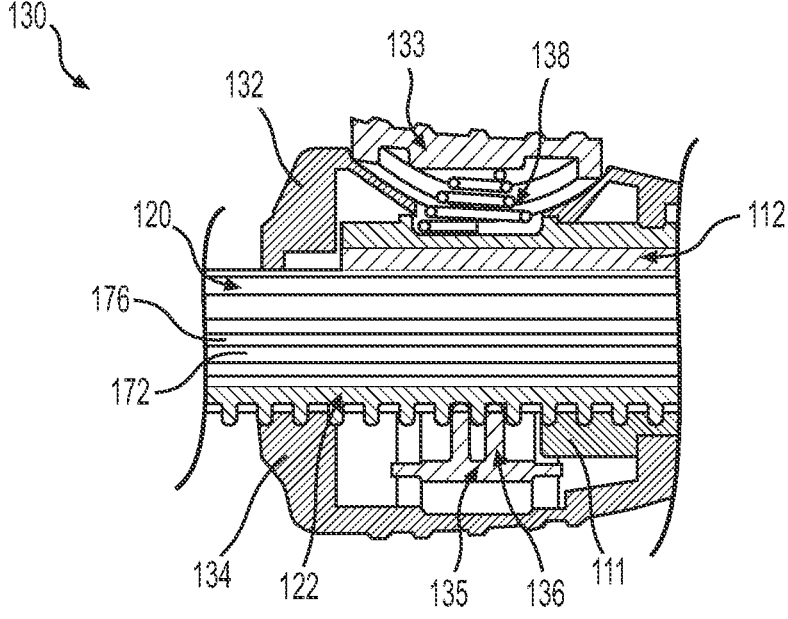
FIG. 4 is a cross-sectional side view of the first actuator of the medical device of FIG. 1 in an actuated state, according to aspects of this disclosure.
Figure 5:
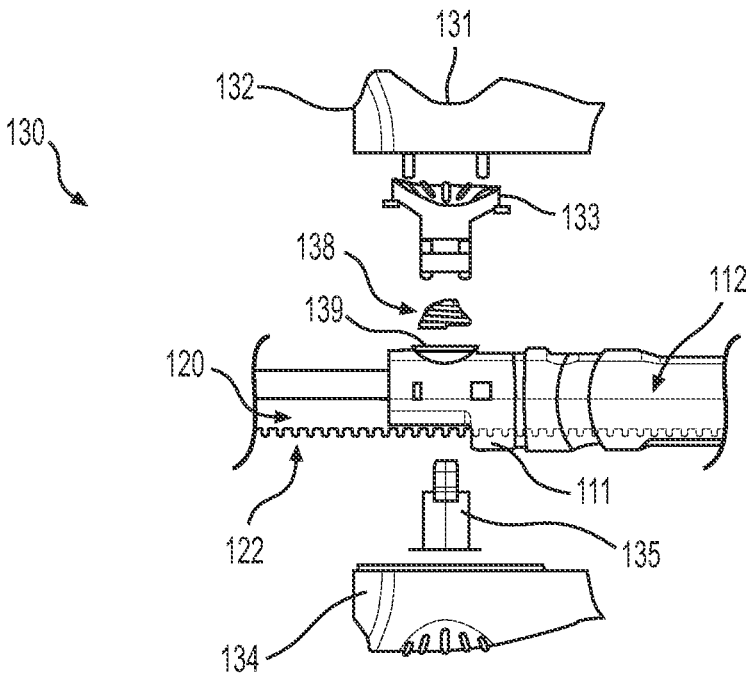
FIG. 5 is an exploded side view of the first actuator of the medical device of FIG. 1, according to aspects of this disclosure.

Referring now to FIGS. 4-5, a schematic of the first actuator 130 is depicted with the outer body 112 and the inner body 120 disposed within the first actuator 130. The first actuator 130 of the medical device 110 is positioned at a distal end 111 of the outer body 112. In the example, a body of the first actuator 130 may include a top housing 132 and a bottom housing 134 coupled to one another with the outer body 112 and the inner body 120 disposed therebetween. Further, the top housing 132 and the bottom housing 134 are positioned relative to the outer body 112 such that at least a portion of the housings 132, 134 are disposed over the distal end 111 of the outer body 112. The first actuator 130 may further include a button top 133 received within the top housing 132 and a button bottom 135 received within the bottom housing 134. It should be understood that the button top 133 and the button bottom 135 of the first actuator 130 may be a unitary structure, such as, for example, a ring disposed about the outer body 112 such that the buttons 133, 135 are integral with one another. In other examples, the button top 133 and the button bottom 135 may be coupled to one another thereby forming an assembly, such that movement of the button top 133 and/or the button bottom 135 provides for a corresponding movement of the opposing button 133, 135.

The top housing 132 of the first actuator 130 includes a recess 131 for receiving the button top 133 such that the button top 133 extends at least partially outward from the top housing 132. In this instance, the button top 133 is partially exposed at the recess 131 to facilitate access to the button top 133 for actuation by a user of the medical device 110. The button bottom 135 of the first actuator 130 is disposed within the bottom housing 134 such that the button bottom 135 is entirely enclosed therein. In other examples, the button bottom 135 may extend at least partially outward from the bottom housing 134 to thereby expose the button bottom 135 therefrom. As described above, the button top 133 and the button bottom 135 of the first actuator 130 form a unitary structure such that the button bottom 135 is configured to move simultaneously with the button top 133. Accordingly, a manual depression of the button top 133 (e.g., toward the outer body 112) may provide a simultaneous depression and/or movement of the button bottom 135 (e.g., away from the outer body 112) when actuating the first actuator 130.

Still referring to FIGS. 4-5, the first actuator 130 may further include a biasing mechanism 138. In the example, the biasing mechanism 138 includes a spring disposed in the top housing 132, for example, the biasing mechanism 138 is positioned between the button top 133 and an exterior surface of the outer body 112. More specifically, an exterior of the outer body 112 includes a cavity 139 adjacent to the distal end 111 of the outer body 112 that is sized and shaped to receive the biasing mechanism 138 therein. In other examples, the biasing mechanism 138 may include various other suitable devices than those shown and described herein without departing from a scope of this disclosure. With the biasing mechanism 138 disposed underneath the button top 133, it should be understood that, in a resting state, the biasing mechanism 138 is configured to apply a radially outward force against the button top 133 (e.g., away from the outer body 112). Accordingly, the button top 133 is biased to an extended position (i.e., an unactuated state) by the biasing mechanism 138, as shown in FIG. 4. As described in greater detail herein, a depression of the first actuator 130 may be provided in response to applying a radially-inward directed force onto the button top 133 that exceeds a radially-outward force generated by the biasing mechanism 138.

Referring now to FIG. 4, the button bottom 135 of the first actuator 130 may include one or more teeth 136 extending outwardly therefrom and toward the rack portion of the inner body 120. For example, with the first actuator 130 disposed and/or extending at least partially over the distal end 111 of the outer body 112, the one or more teeth 136 of the button bottom 135 may be configured to engage at least some of the plurality of teeth 122 (i.e. the rack portion) of the inner body 112 that are positioned adjacent to the distal end 111. In the example, the button bottom 135 of the first actuator 130 includes a pair of teeth 136, however, it should be understood that in other examples the button bottom 135 may include additional and/or fewer teeth 136. Since the button top 133 and the button bottom 135 are connected to one another, it should be appreciated that the biasing mechanism 138 is configured to bias the button bottom 135 and the one or more teeth 136 located thereon to a locked position.

As described in greater detail herein, the first actuator 130 is configured such that the teeth 136 of the button bottom 135 engage the plurality of teeth 122 of the inner body 120 when the first actuator 130 is in an unactuated and resting state (i.e., an undepressed position), as shown in FIG. 4. In this instance, with the teeth 136 of the first actuator 130 engaged (interlocked) with one or more of the plurality of teeth 122 of the inner body 120, a position of the outer body 112 (which the first actuator 130 is secured to) is fixed longitudinally relative to the inner body 120. Accordingly, it should be appreciated that actuation of the first actuator 130 (i.e., manual depression of the button top 133) may allow the teeth 136 of the button bottom 135 to move radially away from and disengage the plurality of teeth 122 of the inner body 120. In this instance, with the first actuator 130 disengaged from the inner body 120, the first actuator 130 may move (e.g., translate) the outer body 112 relative to the inner body 120. Upon release of the radially-inward directed force on the button top 133 of the first actuator 130, the biasing mechanism 138 urges the button bottom 135 back to a locked position with the one or more teeth 136 engaged with at least some of the plurality of teeth 122 on the inner body 120.

Figure 6:
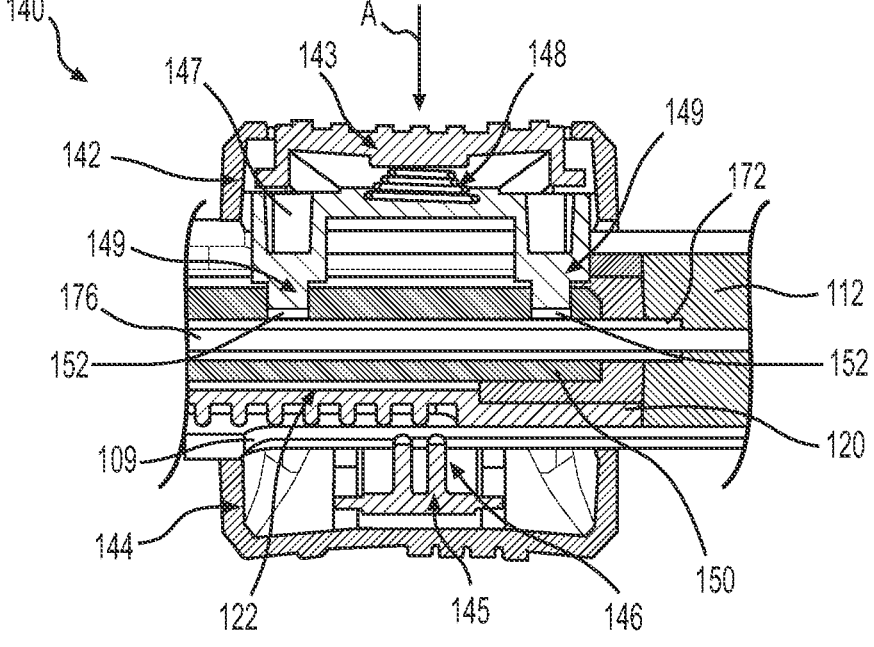
FIG. 6 is a cross-sectional side view of the second actuator of the medical device of FIG. 1 in an unactuated state, according to aspects of this disclosure.
Figure 7:
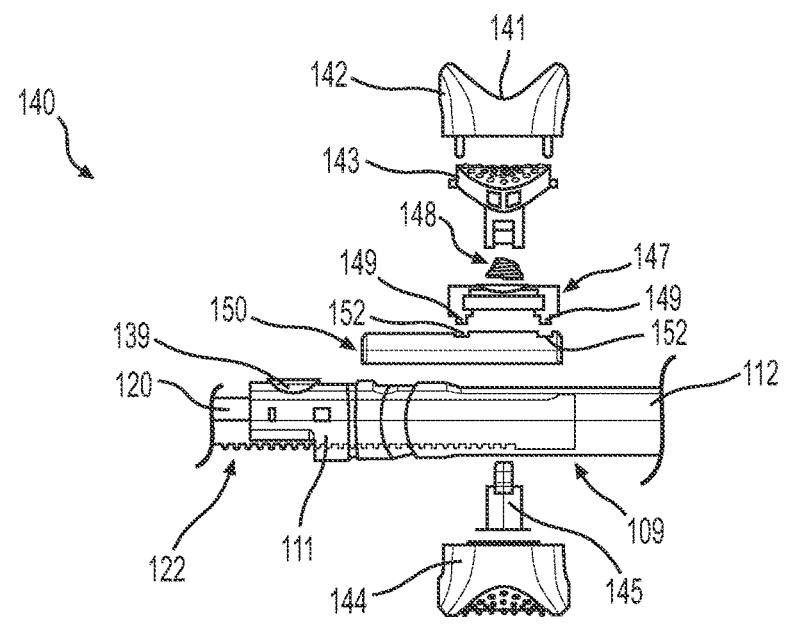
FIG. 7 is an exploded side view of the second actuator of the medical device of FIG. 1, according to aspects of this disclosure.

Referring now to FIGS. 6-7, a schematic of the second actuator 140 is depicted with portions of the outer body 112 and the inner body 120 disposed within the second actuator 140. In the example, a body of the second actuator 140 may include a top housing 142 and a bottom housing 144 coupled to one another with portion of the outer body 112 and the inner body 120 disposed therebetween. The second actuator 140 may further include a button top 143 received within the top housing 142 and a button bottom 145 received within the bottom housing 144. It should be understood that the button top 143 and the button bottom 145 of the second actuator 140 may be a unitary structure, such as, for example, a ring disposed about the outer body 112, such that the buttons 143, 145 are integral with one another. In other examples, the button top 143 and the button bottom 145 may be coupled to one another thereby forming an assembly, such that movement of the button top 143 and/or the button bottom 145 provides for a corresponding movement of the opposing button 143, 145.

The top housing 142 of the second actuator 140 includes a recess 141 for receiving the button top 143, such that the button top 143 extends at least partially outward from the top housing 142. In this instance, the button top 143 is partially exposed at the recess 141 to facilitate access to the button top 143 for actuation by a user of the medical device 110. The button bottom 145 of the second actuator 140 is disposed within the bottom housing 144 such that the button bottom 145 is enclosed entirely therein. In other examples, the button bottom 145 may extend at least partially outward from the bottom housing 144 to thereby expose the button bottom 145 therefrom. As described above, the button top 143 and the button bottom 145 of the second actuator 140 form a unitary structure such that the button bottom 145 is configured to move simultaneously with the button top 143. Accordingly, a manual depression of the button top 143 (e.g., toward the outer body 112) may provide a simultaneous depression and/or movement of the button bottom 145 (e.g., away from the outer body 112) when actuating the second actuator 140.

Still referring to FIGS. 6-7, the second actuator 140 may further include a biasing mechanism 148. In the example, the biasing mechanism 148 includes a spring disposed in the top housing 142, for example, the biasing mechanism 148 is positioned between the button top 143 and a retainer 147 of the second actuator 140. In other examples, the biasing mechanism 148 may include various other suitable devices than those shown and described herein without departing from a scope of this disclosure. With the biasing mechanism 148 disposed underneath the button top 143, it should be understood that the biasing mechanism 148 is configured to apply a radially-outward force against the button top 143 (e.g., away from the outer body 112). Accordingly, the button top 143 is biased to an extended position such that a manual depression of the second actuator 140 may be provided in response to applying a radially-inward force onto the button top 143 (e.g., in a direction A) that exceeds the radially-outward force generated by the biasing mechanism 148. As described further herein, depression of the second actuator 140 provides for a disengagement of the button bottom 145 with the inner body 120.

The retainer 147 is at least partially disposed within the top housing 142 of the second actuator 140 and is positioned between the button top 143 and the outer body 112. The retainer 147 is configured to receive the biasing mechanism 148 along a top surface of the retainer 147 and includes one or more engagement features 149 positioned along a bottom surface of the retainer 147. The one or more engagement features 149 may include protrusions that extend outwardly from a bottom surface of the retainer 147. In the example, the engagement features 149 of the retainer 147 are received in a lumen of the inner body 120 via the slot 109 formed along a top surface of the outer body 112 and the slot 124 formed along a top surface of the inner body 120 (see FIG. 2). It should be appreciated that the slots 109, 124 of the outer body 112 and the inner body 120 may overlap the radially-aligned, and/or be positioned coincident to one another such that the engagement features 149 of the retainer 147 extend through a respective pair of slots 109, 124 and into a lumen of the inner body 120.

Still referring to FIGS. 6-7, the second actuator 140 may further include a sled 150 disposed within a lumen of the inner body 120. In the example, the sled 150 includes one or more apertures 152 formed along a top surface of the sled 150. A size, shape, and quantity of the apertures 152 may correspond to the one or more engagement features 149 (e.g., protrusions) of the retainer 147. Accordingly, the retainer 147 is configured to couple the button top 143 to the sled 150 via receipt of the engagement features 149 within the apertures 152. In the example, the sled 150 is disposed about and secured to the medical instrument 170, for example, the sheath 172. For example, the sled 150 may be attached to the sheath 172 of the medical instrument 170 by an adhesive such that the sled 150 is fixed relative to the medical instrument 170. In this instance, the medical instrument 170 is movable relative to a lumen of the inner body 120 in response to movement of the sled 150, such as, for example, via movement of the second actuator 140. It should be understood that, in other examples, the sled 150 may be attached to the sheath 172 of the medical instrument 170 by various other devices and/or mechanisms suitable for fixing the sled 150 to the medical instrument 170.

Referring now to FIG. 6, the button bottom 145 of the second actuator 140 may include one or more teeth 146 extending outwardly therefrom and toward the rack portion of the inner body 120. For example, with the second actuator 140 disposed and/or extending over the outer body 112, the one or more teeth 146 of the button bottom 145 may be configured to engage at least some of the plurality of teeth 122 (i.e. the rack portion) of the inner body 112 through the slot 109 formed along a bottom surface of the outer body 112. In the example, the button bottom 145 of the second actuator 140 includes a pair of teeth 146, however, it should be understood that in other examples the button bottom 145 may include additional and/or fewer teeth 146. Since the button top 143 and the button bottom 145 are connected to one another, it should be appreciated that the biasing mechanism 148 is configured to bias the button bottom 145 and the one or more teeth 146 located thereon to a locked position.

As described in greater detail herein, the second actuator 140 is configured such that the teeth 146 of the button bottom 145 are engaged with the plurality of teeth 122 of the inner body 120 when the second actuator 140 is in an unactuated and resting state (i.e., an undepressed position). In this instance, with the teeth 146 of the second actuator 140 engaged (interlocked) with one or more of the plurality of teeth 122 of the inner body 120, a position of the inner body 120 is fixed longitudinally relative to the outer body 112 and the sheath 172. Accordingly, it should be appreciated that actuation of the second actuator 140 (i.e., manual depression of the button top 143 in a direction A) may allow the teeth 146 of the button bottom 145 to move radially away from and disengage the plurality of teeth 122 of the inner body 120. In this instance, with the second actuator 140 disengaged from the inner body 120, the second actuator 140 may move (e.g., translate) the sheath 172 of the medical instrument relative to the outer body 112, the inner body 120, and/or the cannula 176. Upon release of the radially-inward directed force on the button top 143 of the second actuator 140, the biasing mechanism 148 urges the button bottom 145 back to a locked position with the one or more teeth 146 engaged with at least some of the plurality of teeth 122 on the inner body 120.

According to an exemplary method of using the medical system 100, the medical system 100 may be utilized in various endoscopic procedures to treat a target site (e.g., patient anatomy). Initially, the medical instrument 170 may be received within the medical device 110 with at least a distal portion of the sheath 172 extending distally from the distal housing 160. The tip 178 of the cannula 176 may be disposed within the sheath 172 of the medical instrument 170 by positioning the first actuator 130 at and/or near a proximal portion of the inner body 120, as shown in FIG. 1. Further, the sheath 172 of the medical instrument 170 may be disposed over the tip 178 of the cannula 176 by positioning the second actuator 140 at and/or near the distal end 111 of the outer body 112, as shown in FIG. 1. In this instance, with the needle 179 received within a lumen of the cannula 176 and extending at least partially outward therefrom via the tip 178, the tip 174 of the sheath 172 may enclose a distal tip of the needle 179 therein.

Upon positioning the medical system 100 at and/or near a target site, a user of the medical system 100 may actuate one or more components of the medical system 100 to utilize the components of the medical instrument 170 (e.g., the sheath 172, the cannula 176 and/or the needle 179) at the target site. In examples where the sheath 172 includes an electrosurgical sheath and the tip 174 includes an electrosurgical tip, the sheath 172 and/or the tip 174 may be operable to electrosurgically dilate and/or ablate the target site in response to actuation of an ancillary device (e.g., an electrosurgical generator) coupled to the medical instrument 170 via the active pin 116.

By way of further example, a user may actuate the second actuator 140 by applying a radially-inward force (e.g., transverse to a longitudinal length of the outer body 112) onto the button top 143 to depress the biasing mechanism 148 and disengage the teeth 146 of the button bottom 145 from the plurality of teeth 122 of the inner body 120. It should be appreciated that the radially-inward force should be greater than an opposing, radially-outward biasing force applied against the button top 143 of the second actuator 140 by the biasing mechanism 148. In this instance, with the second actuator 140 disengaged from the inner body 120, a user may move the second actuator 140 relative to the outer body 112 by applying a slidable force (e.g., parallel to a longitudinal length of the outer body 112) onto the second actuator 140.

With the sled 150 secured to the sheath 172 of the medical instrument 170 and the second actuator 140 secured to the sled 150 via the retainer 147 (see FIGS. 6-7), movement of the second actuator 140 provides a simultaneous movement of the sheath 172 relative to the outer body 112, the inner body 120, and the cannula 176. Accordingly, movement of the second actuator 140 from the distal end 111 of the outer body 112 (see FIG. 1) toward a proximal portion of the outer body 112 (e.g., adjacent to the end cap 114) provides a retraction of the sheath 172 into a lumen of the outer body 112, exposing the cannula 176 and the needle 179. In this instance, the tip 174 of the sheath 172 may be positioned proximally relative to a distal tip of the needle 179 and the tip 178 of the cannula 176 for use at the target site during a procedure (see FIG. 8).

A user may lock the second actuator 140 by releasing the button top 143 to thereby fix a position of the second actuator 140 relative to the outer body 112, and in result a position of the sheath 172 and the tip 174 relative to the cannula 176 and the needle 179. For example, removing the radially-inward force from the button top 143 allows the biasing force of the biasing mechanism 148 to supersede, thereby returning the second actuator 140 to an unactuated state wherein the teeth 146 of the button bottom 145 engage at least some of the plurality of teeth 122 of the inner body 120. Accordingly, a position of the second actuator 140 relative to the outer body 112, and a position of the sheath 172 relative to the cannula 176 and the needle 179, remains fixed without requiring continued actuation (e.g., depression) of the second actuator 140 by a user. With a distal tip of the needle 179 exposed from within the sheath 172, a user may direct the needle 179 toward a target treatment site to puncture the target site with the distal tip of the needle 179.

With the target site dilated, ablated, and/or punctured by the medical instrument 170, a user may further actuate the medical system 100 to utilize one or more other components of the medical device 110 and/or the medical instrument 170 at the target site. By way of illustrative example, a user may actuate the first actuator 130 by applying a radially-inward force (e.g., transverse to a longitudinal length of the outer body 112) onto the button top 133 to depress the biasing mechanism 138 and disengage the teeth 136 of the button bottom 135 from the plurality of teeth 122 of the inner body 120. It should be appreciated that the radially-inward force should be greater than an opposing biasing force applied against the button top 133 of the first actuator 130 by the biasing mechanism 138.

In this instance, with the first actuator 130 disengaged from the inner body 120, a user may move the outer body 112 relative to the inner body 120 by applying a slidable force (e.g., parallel to a longitudinal length of the outer body 112) onto the first actuator 130. With the rotation assembly 118 secured to the cannula 176 of the medical instrument 170 and the outer body 112 secured to the rotation assembly 118, movement of the first actuator 130 provides a simultaneous movement of the rotation assembly 118 and the cannula 176 relative to the sheath 172. Accordingly, actuation of the first actuator 130 allows for the tip 178 of the cannula 176 to move relative to the tip 174 of the sheath 172, and/or relative to the target site. In this instance, the tip 178 of the cannula 176 may be extended distally relative to the tip 174 of the sheath 172 by translating the first actuator 130 distally along the inner body 120 to position a distal tip of the needle 179 at another location at the target site to puncture the target site, for example. Additionally and/or alternatively, the needle 179 may be removed from a lumen of the cannula 176 and replaced with one or more other tools/devices via a lumen of the rotation assembly 118.

A user may lock the first actuator 130 by releasing the button top 133 to thereby fix a position of the outer body 112 relative to the inner body 120, and a position of the cannula 176 relative to the sheath 172. For example, removing the radially-inward force from the button top 133 allows the biasing force of the biasing mechanism 138 to supersede, thereby returning the first actuator 130 to an unactuated state (see FIG. 4) wherein the teeth 136 of the button bottom 135 engage at least some of the plurality of teeth 122 of the inner body 120. Accordingly, a position of the outer body 112 relative to the inner body 120, and the cannula 176 relative to the sheath 172 of the medical instrument 170, remains longitudinally fixed without requiring continued actuation (e.g., depression) of the first actuator 130 by a user.

Upon puncturing a target site with the cannula 176 and the needle 179, a user may actuate the first actuator 130 and/or the second actuator 140 to redispose the cannula 176 and the needle 179 within a lumen of the sheath 172. For instance, the first actuator 130 may be actuated, as described in detail above, and moved proximally relative to the inner body 120 to retract the cannula 176 and the needle 179 into the sheath 172. Alternatively, the second actuator 140 may be actuated, as described above, and moved distally relative to the outer body 112 to extend the tip 174 of the sheath 172 over the cannula 176 and the needle 179. In such instances, with the cannula 176 and the needle 179 fully disposed within a lumen of the sheath 172, a user may utilize the sheath 172 during a procedure. Further actuation of the medical system 100 may be performed by a user during a procedure to utilize components of the medical device 110 and/or the medical instrument 170 at the target site, such as, for example, actuating the first actuator 130 and/or the second actuator 140 in accordance with the steps described above. It should be understood that the steps described herein, and the sequence in which they are presented, are merely illustrative such that additional and/or fewer steps may be included without departing from a scope of this disclosure.

FIG. 8 shows a schematic depiction of an exemplary medical system 200 in accordance with an example of this disclosure. Except as otherwise described below, it should be understood that the medical system 200 may be configured and operable like the medical system 100 shown and described above such that like reference numerals are used to identify like components. Accordingly, it should be appreciated that the medical system 200 functions similar to the medical system 100 except for the differences explicitly noted herein.

For example, the medical system 200 may include a medical device 210 and the medical instrument 170 at least partially disposed within the inner body 120 of the medical device 210. The outer body 112 of the medical device 210 may include the first actuator 130 and a second actuator 240 disposed along an exterior of the outer body 112. In the example, the second actuator 240 is substantially similar to the second actuator 140 of the medical system 100 shown and described above except for the second actuator 240 including an active pin (connector) 216 extending outwardly therefrom.

Referring now to FIGS. 9-10, a bottom housing 244 of the second actuator 240 includes a port 212 that is sized and shaped in accordance with the active pin 216 such that the bottom housing 244 is configured to receive the active pin 216 through the port 212. It should be understood that the active pin 216 of the medical device 210 is configured and operable similar to the active pin 116 of the medical device 110 shown and described above. In this instance, the active pin 216 of the medical device 210 is received in a lumen of the inner body 120, and coupled to the medical instrument 170 disposed therein, via the second actuator 240. A connector 217 of the active pin 216 is received within the bottom housing 244 of the second actuator 240 through the port 212, rather than in the end cap 114 as shown and described above with respect to the medical device 110 of the medical system 100.

Accordingly, it should be appreciated that the active pin 216 of the medical device 210 is operable to move relative to the outer body 112 in response to a movement of the second actuator 240 relative to the outer body 112. In this instance, the active pin 216 remains adjacent to the sheath 172 of the medical instrument 170 during use of the medical system 200 in a procedure, such as, for example, when the sheath 172 is moved relative to the outer body 112, the inner body 120, and the like.

Each of the aforementioned devices, assemblies, and methods may be used to facilitate access to a target treatment site and provide enhanced control of ancillary tools/devices for use at the target treatment site. By providing a medical device with a pair of actuators capable of controlling and automatically locking a plurality of tools/devices of a medical instrument coupled to the medical device, a user may interact with a target treatment site using the various tools/devices of the medical instrument during a procedure without requiring continued manual control of the medical device. In this instance, a user may reduce overall procedure time, increase efficiency of procedures, and/or avoid unnecessary harm to a patient's body caused by limited control of the ancillary tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A handle of a medical device, comprising:
an outer body;
an inner body, wherein at least a portion of the inner body is movably disposed within the outer body;
an actuator, wherein the actuator has an actuated state permitting movement of the outer body relative to the inner body; and
a biasing mechanism disposed between the actuator and the outer body and within a cavity of the outer body, wherein the biasing mechanism is configured to (i) bias the actuator radially outward relative to the outer body and (ii) bias the actuator towards an unactuated state;
wherein the unactuated state of the actuator inhibits movement of the outer body relative to the inner body.

2. The handle of claim 1, further comprising:
a sheath extending from the handle; and
a tool movably disposed within the sheath, wherein the actuator is secured to the tool, and wherein the actuated state of the actuator permits movement of the tool relative to the sheath, and wherein the unactuated state of the actuator inhibits movement of the tool relative to the sheath.

3. The handle of claim 2, wherein the tool is a needle.

4. The handle of claim 1, wherein the actuator is a first actuator and the biasing mechanism is a first biasing mechanism, and wherein the handle comprises a second actuator and a second biasing mechanism, wherein the second biasing mechanism is disposed between the second actuator and the outer body, and wherein the second biasing mechanism is configured to (i) bias the second actuator radially outward relative to the outer body and (ii) bias the second actuator towards an unactuated state.

5. The handle of claim 4, wherein longitudinal movement of the first actuator moves the outer body longitudinally relative to the second actuator, and wherein longitudinal movement of the second actuator is configured to move a sheath longitudinally relative to the inner body and the outer body.

6. The handle of claim 4, further comprising:
a sled including an aperture;
a retainer including a protrusion that is received within the aperture to couple the retainer to the sled, wherein the second biasing mechanism is disposed between the second actuator and the retainer, wherein the second biasing mechanism is configured to bias the second actuator radially outward relative to the retainer and maintain the second actuator in the unactuated state.

7. The handle of claim 6, wherein an engagement feature of the retainer is received within the aperture.

8. The handle of claim 1, wherein the inner body includes a plurality of teeth extending along a portion of the inner body; and
wherein the actuator includes one or more teeth disposed entirely radially within a housing of the actuator, wherein the one or more teeth are of the actuator are configured to engage one or more of the plurality of teeth of the inner body when in the unactuated state.

9. The handle of claim 8, wherein the plurality of teeth of the inner body is disposed on a first side of the inner body, and wherein the biasing mechanism is disposed on a second side of the inner body, opposite the first side.

10. The handle of claim 1, wherein the biasing mechanism is a spring.

11. The handle of claim 1, wherein the inner body extends proximally relative to the outer body.

12. The handle of claim 1, wherein the actuator includes a button.

13. The handle of claim 1, wherein the inner body includes a pair of slots, wherein each slot of the pair of slots extends longitudinally along the inner body, wherein each slot of the pair of slots is positioned on an opposite side of the inner body, wherein the pair of slots is configured to slidably receive the actuator.

14. The handle of claim 1, further comprising a rotation assembly coupled to the outer body, wherein the rotation assembly is configured to rotate a medical instrument relative to the inner body and the outer body.

15. A handle of a medical device, comprising:
a first body;
a second body, wherein at least a portion of the second body is movably disposed within the first body;
an actuator, wherein the actuator has an actuated state permitting movement of the first body relative to the second body and an unactuated state inhibiting movement of the first body relative to the second body, wherein the actuator is configured to engage with the second body in the unactuated state;

a spring disposed between the actuator and the second body and within a cavity of the first body, wherein the spring is configured to (i) bias the actuator radially outward relative to the first body and (ii) bias the actuator towards an unactuated state.

16. The handle of claim 15, further comprising:

a sheath extending from the handle; and a needle movably disposed within the sheath, wherein the actuator is secured to the needle, and wherein the actuated state of the actuator permits movement of the needle relative to the sheath, and wherein the unactuated state of the actuator inhibits movement of the needle relative to the sheath.

17. The handle of claim 15, wherein the actuator includes one or more teeth disposed entirely radially within a housing of the actuator, wherein the second body includes a plurality of teeth extending along a portion of the second body, wherein the plurality of teeth of the second body is disposed on a first side of the second body, and wherein the spring is disposed on a second side of the second body, opposite the first side, and wherein, in the unactuated state, the one or more teeth of the actuator are configured to engage one or more of the plurality of teeth of the second body in the unactuated state.

18. The handle of claim 15, wherein the actuator is a first actuator and the spring is a first spring, and wherein the handle comprises a second actuator and a second spring, wherein the second spring is disposed between the second actuator and the first body, and wherein the second spring is configured to (i) bias the second actuator radially outward relative to the first body and (ii) bias the second actuator towards an unactuated state.

19. A medical device, comprising:

a handle;

a sheath extending from the handle; and a needle within the sheath and movable relative to the sheath;

wherein the handle includes:

an inner body;

an outer body disposed over the inner body, wherein the outer body is movable relative to the inner body;

an actuator, wherein the actuator has an actuated state permitting movement of the outer body relative to the inner body and an unactuated state inhibiting movement of the outer body relative to the inner body, wherein the actuator is configured to engage the outer body in the unactuated state, and wherein the unactuated state of the actuator inhibits movement of the needle relative to the sheath; and a spring disposed between the actuator and the outer body and within a cavity of the outer body, wherein the spring is configured to (i) bias the actuator radially outward relative to the outer body and (ii) bias the actuator towards an unactuated state.

20. The handle of claim 19, wherein the actuator includes a button.

* * * * *